United States Patent [19]

Blom et al.

[11] Patent Number: 4,911,716

[45] Date of Patent: Mar. 27, 1990

[54] SURGICAL IMPLANT FOR A VOICE PROSTHESIS

[75] Inventors: Eric D. Blom, Indianapolis; Mark I. Singer, Carmel, both of Ind.

[73] Assignee: Hansa Medical Products, Inc., Indianapolis, Ind.

[21] Appl. No.: 336,842

[22] Filed: Apr. 12, 1989

Related U.S. Application Data

[63] Continuation-in-part of Ser. No. 192,246, May 9, 1988, which is a continuation of Ser. No. 51,133, May 18, 1987, which is a continuation-in-part of Ser. No. 916,310, Oct. 7, 1986, which is a continuation-in-part of Ser. No. 894,274, Aug. 7, 1986, which is a continuation-in-part of Ser. No. 786,508, Oct. 11, 1985, which is a continuation-in-part of Ser. No. 572,249, Jan. 20, 1984, Pat. No. 4,614,516, which is a continuation-in-part of Ser. No. 373,635, Apr. 30, 1982, Pat. No. 4,435,853.

[51] Int. Cl.$^4$ .............................................. A61F 2/20
[52] U.S. Cl. ................................... 623/9; 128/200.26; 604/264
[58] Field of Search ................. 623/9; 604/9, 10, 247, 604/264, 282; 128/200.26, 207.14, 207.15

[56] References Cited

U.S. PATENT DOCUMENTS

| | | |
|---|---|---|
| 155,667 | 10/1874 | Painter . |
| 3,137,299 | 6/1964 | Tabor . |
| 3,169,529 | 2/1965 | Koenig . |
| 3,263,684 | 8/1966 | Bolton . |
| 3,499,450 | 3/1970 | Rathjen . |
| 3,747,127 | 7/1973 | Taub . |
| 3,844,290 | 10/1974 | Birch et al. . |
| 3,952,335 | 4/1976 | Sorce et al. . |
| 4,044,402 | 8/1977 | Edwards . |
| 4,269,184 | 5/1981 | Montgomery . |
| 4,274,162 | 6/1981 | Joy et al. . |
| 4,325,366 | 4/1982 | Tabor . |
| 4,435,853 | 3/1984 | Blom et al. . |
| 4,475,888 | 10/1984 | Gores et al. . |
| 4,596,579 | 6/1986 | Pruitt . |
| 4,614,516 | 9/1986 | Blom et al. . |
| 4,653,496 | 3/1987 | Bundy ................................ 604/264 |
| 4,820,304 | 4/1989 | Depel ..................................... 623/9 |

OTHER PUBLICATIONS

Singer, Mark I., M.D. and Eric D. Blom, PhD, "An Endoscopic Technique For Restoration of Voice After Laryngectomy", reprint from *Annals of Otology, Phinology And Laryngology*, vol. 89, No. 6, Nov.-Dec. 1980, pp. 529-533.

Mahieu, H. F., et al., "*Candida* Vegetations on Silicon Voice Prostheses", Arch. Otolaryngol. Head Neck Surg., Mar. 1986, vol. 112, pp. 321-325.

"Artery-Expanding Stents Widen Hopes for Patients with Atherosclerosis", Medical New & Perspectives, *JAMA*, Jan. 15, 1988, vol. 259, pp. 327-329.

Dotter, Charles D., M.D., "Transluminally-Placed Coilspring Endarterial Tube Grafts", *Investigative Radiology*, Sep.-Oct., 1969, pp. 329-332.

Maass, D., et al., "Radiological Follow-up of Transluminally Inserted Vascular Endoprostheses: An Ex-

(List continued on next page.)

Primary Examiner—Richard J. Apley
Assistant Examiner—James Prizant
Attorney, Agent, or Firm—Barnes & Thornburg

[57] ABSTRACT

A surgical implant for use in voice restoration comprises a length of coiled spring. The length of coiled spring has a first end adapted for positioning adjacent the anterior wall of the esophagus of the wearer of the surgical implant and a second end adapted for positioning adjacent the posterior wall of the trachea. A voice prosthesis device for use with the surgical implant comprises a right circular cylinder, the outside diameter of which is substantially equal to the inside diameter of the length of coiled spring. This permits insertion of the voice prosthetic device from the tracheal end of the implant thereinto, as well as removal of the voice prosthetic device for cleaning, repair, or replacement. The voice prosthetic device contains a one-way valve permitting air flow from the tracheal end thereof to the esophageal end thereof, to provide the wearer with esophageal speech.

10 Claims, 6 Drawing Sheets

OTHER PUBLICATIONS perimental Study Using Expanding Spirals", *Radiology*, Sep. 1984, pp. 659–663.

Rousseau, Herve, M.D., et al., "Self-Expanding Endovascular Prosthesis: An Experimental Study", *Radiology*, Sep. 1987, pp. 709–714.

Palmax, Julio C., M.D., et al., "Normal and Stenotic Renal Arteries: Experimental Balloon-Expandable Intraluminal Stenting", *Radiology*, Sep. 1987, pp. 705–708.

Palmaz, Julio C., M.D., et al., "Expandable Intraluminal Graft: A Preliminary Study", *Radiology*, 1985, pp. 73–77.

Wallace, Michael J., et al., "trachobronchial Tree: Expandable Metallic Stents Used in Experimental and Clinical Applications", *Radiology*, 1986, pp. 309–312.

Wright, Kenneth C., Ph.D., et al., "Percutaneous Endovascular Stents: An Experimental Evaluation", *Radiology*, Jul. 1985, pp. 69–72.

Duprat, Gerard, Jr., M.D., et al., "Self-Expanding Metallic Stents for Small Vessels: An Experimental Evaluation", *Radiology*, Feb. 1987, pp. 469–472.

Rollins, Nancy, M.D., et al., "Self-Expanding Metallic Stents: Preliminary Evaluation in an Atherosclerotic Model", *Radiology*, Jun. 1987, pp. 739–742.

Dotter, Charles T., M.D., et al., "Transluminal Expandable Nitinol Coil Stent Grafting: Preliminary Report", *Radiology*, Apr. 1983, pp. 259–260.

Cragg, Andrew, M.D., et al., "Nonsurgical Placement of Arterial Endoprostheses: A New Technique Using Nitinol Wire", *Radiology*, Apr. 1983, pp. 261–263.

SURGICAL IMPLANT FOR A VOICE PROSTHESIS

This is a continuation-in-part of our co-pending U.S.S.N. No. 192,246 filed May 9, 1988 and assigned to the same assignee as the present application. U.S.S.N. No. 192,246 is a continuation of our co-pending U.S.S.N. No. 051,133 filed May 18, 1987 and assigned to the same assignee as the present application. U.S.S.N. No. 051,133 is a continuation-in-part of our co-pending U.S.S.N. No. 916,310, filed Oct. 7, 1986 and assigned to the same assignee as the present application. U.S.S.N. No. 916,310 is a continuation-in-part of our co-pending U.S.S.N. No. 894,274, filed Aug. 7, 1986 and assigned to the same assignee as the present application. U.S.S.N. No. 894,274 is a continuation-in-part of our co-pending U.S.S.N. No. 786,508, filed Oct. 11, 1985 and assigned to the same assignee as the present application. U.S.S.N. No. 786,508 is a continuation-in-part of our co-pending U.S.S.N. No. 572,249, filed Jan. 20, 1984 now U.S. Pat. No. 4,614,516. U.S.S.N. No. 572,249 is a continuation-in-part of our co-pending U.S.S.N. No. 373,635, filed Apr. 30, 1982 now U.S. Pat. No. 4,435,853.

This invention relates to surgical implants, and more particularly to a surgical implant for use with voice prosthesis devices of the general types described in U.S. Pat. Nos. 4,435,853 and 4,614,516.

Voice prosthesis devices of these types are generally constructed from relatively soft, pliable biocompatible materials. These devices become contaminated with food particles, mucus, saliva and certain species of Candida, flora that occasionally infect mucus membranes of the throat and trachea. See, Mahieu, H.F., et al., "Candida Vegetations on Silicone Voice Prostheses," *Arch. Otolaryngol. Head Neck Surg.*, Mar. 1986, Vol. 112, pp. 321–325. Consequently, it is not uncommon for a wearer of a voice prosthesis device of these general types to have to remove the device, for cleaning or for replacement.

In such users, it is not uncommon for the device to be out of the user's fistula for a period of up to five to ten minutes during which time either an alternative prosthesis put in its place or a catheter is put in to maintain the fistula. If the user fails to maintain the fistula at all times, it will close rapidly, even in as short a time as five to ten minutes, to the point that the patient cannot get the device back into the fistula. This requires that another surgical operation be performed to reopen the fistula so that the cleaned voice prosthesis device or a new voice prosthesis device can be inserted. Some surgeons have expressed a reluctance to use voice prosthesis devices of these general types because of this propensity of the fistula to reclose when the voice prosthesis device is removed for regular hygiene, repair or replacement.

Additionally, many patients have found that it is sometimes difficult to replace the voice prosthesis device in the fistula even when the voice prosthesis device is only out for a relatively shorter period of time than that necessary for the fistula to close completely. The fistula prolapses essentially immediately when the voice prosthesis device is removed, and so is somewhat smaller even when the device has not been out of the fistula for too long a period of time.

The use of coil springs to stent blood vessels is known. See, for example, "Artery-Expanding Stents Widen Hopes for Patients with Atherosclerosis," Medical News & Perspectives, *JAMA*, Jan. 15, 1988 Vol. 259, pp. 327–329.

It is an object of the present invention to ease hygiene and replacement of voice prosthesis devices of the types discussed above.

As used herein, the term "cylinder" is a body bounded by two ends (the ends of the cylinder) and a surface whose directrix (its projection on either of the two ends) is closed.

According to the invention, a surgical implant is provided for use in voice restoration in a laryngectomee. The implant includes a cylinder of a relatively rigid material for positioning substantially permanently in a fistula between the trachea and the esophagus, and means for retaining the cylinder in the fistula. Illustratively the implant is constructed from a biocompatible material such as titanium, stainless steel or silicone.

According to an illustrative embodiment, the means for retaining the cylinder in the fistula comprises spaced first and second projections, such as flanges, extending radially outwardly from the exterior wall of the cylinder. When the implant is positioned in the fistula, the first projection lies adjacent the anterior wall of the esophagus and the second projection lies adjacent to the posterior wall of the trachea.

Also illustratively, the cylinder comprises an outer cylindrical wall for contacting the tissue of the fistula and an inner cylindrical wall having a first portion of a relatively larger size for positioning toward the esophageal end of the fistula and a second portion of a relatively smaller size for positioning toward the tracheal end of the fistula.

According to another aspect of the invention, a combination of the surgical implant and a voice prosthesis is provided to restore voice in a laryngectomee. The voice prosthesis comprises a second cylinder, means providing a one-way valve adjacent one end of the second cylinder and means providing a passageway for the entry of air into the second cylinder adjacent the other end of the second cylinder. The first-mentioned cylinder slidably receives the second cylinder.

According to this aspect of the invention, the second cylinder further comprises a radial projection between its ends. The first-mentioned cylinder comprises an outer cylindrical wall for contacting the tissue of the fistula and an inner cylindrical wall having a first portion of a relatively larger size, a second portion of a relatively smaller size and a transition region between the first and second portions. The first portion lies closer to the esophageal end of the surgical implant and the second portion lies closer to the tracheal end of the surgical implant. The radial projection on the second cylinder lies in the first portion when the voice prosthesis is in its use orientation in the surgical implant.

Illustratively, the first-mentioned cylinder comprises a biocompatible metal, such as stainless steel or titanium, and the second cylinder comprises silicone. Alternatively, the second cylinder comprises a relatively softer, more pliable and resilient silicone and the first-mentioned cylinder comprises a relatively harder, less pliable and more rigid silicone.

According to this embodiment of the invention, the means for retaining the implant in the fistula comprises spaced, first and second radially outwardly extending projections on the first-mentioned cylinder, the first projection lying adjacent the anterior wall of the esophagus and the second projection lying adjacent the posterior wall of the trachea when the implant is positioned in the fistula. Illustratively, these projections are flanges. Illustratively, these flanges are provided at the opposite ends of the first-mentioned cylinder.

According to another aspect of the invention, a surgical implant for use in voice restoration comprises multiple coils of a resilient material. The coils define an axis and two ends. First means is provided at a first one of the ends for positioning adjacent the anterior wall of the esophagus of wearer of the surgical implant. Second means is provided at the second end for positioning adjacent the posterior wall of the trachea of the wearer.

According to an illustrative embodiment, the second means comprises a nut having a passageway for receiving at least one of the coils. The passageway has internal threads for threadably engaging at least one of the coils.

Illustratively according to one embodiment, the nut has two opposed faces, a first of which faces axially of the coils toward the posterior wall of the trachea when the nut threadably engages the coil, and a second of which faces axially of the coils away from the posterior wall of the trachea when the nut threadably engages the coil.

Further illustratively according to this embodiment, the nut further comprises means providing a second passageway extending between the first and second faces thereof. A voice prosthesis device comprises a cylinder defining an axis, a first end for positioning adjacent the first end of the coils and a second end for positioning adjacent the second end of the coils. The cylinder includes means defining a passageway therethrough between the first and second ends thereof. A one-way valve is provided within the voice prosthesis device passageway, and a flange extends radially outwardly adjacent the second end of the voice prosthesis device cylinder. The flange has two opposed faces, one facing axially toward the posterior wall of the trachea when the voice prosthesis device is positioned in the implant and a second facing axially away from the posterior wall of the trachea when the voice prosthesis device is positioned in the implant. The flange includes means defining a passageway extending therethrough between the first and second faces of the voice prosthesis device flange for alignment with the second passageway through the nut.

Illustratively, the voice prosthesis device cylinder and flange are constructed from a biocompatible metal. The voice prosthesis device one-way valve comprises a valve seat facing the first end and extending radially inwardly of the voice prosthesis device cylinder into the voice prosthesis device passageway, a valve closure for seating against the one-way valve seat, and means for attaching the valve closure in operative position within the voice prosthesis device passageway adjacent the one-way valve seat.

According to an illustrative embodiment of the invention, the one-way valve closure comprises a sheet of resilient, flexible biocompatible material for providing a hinge. The sheet of resilient, flexible biocompatible material has a first surface facing toward the one-way valve seat, an opposed second surface facing toward the first end of the voice prosthesis device, and sheets of biocompatible metal for shielding the first and second surfaces of the sheet of resilient flexible biocompatible material.

According to yet another aspect of the invention, a method is provided of inserting a surgical implant into a tracheoesophageal fistula. The implant comprises multiple coils of a resilient material. The coils define an axis and two ends. The projection of the coils onto either of the two ends is generally circular. First means is provided at a first end for positioning adjacent the anterior wall of the esophagus of a wearer of the surgical implant to prevent the implant from working back through the fistula to the tracheal end thereof. The first means extends radially outward from the coil axis beyond the generally circular projection of the coils onto the first end. The method comprises the steps of providing a sleeve of a water soluble material, the sleeve having a first open end and a second tapered or rounded end. The first means or coils are deformed to permit insertion of the first means into the first end of the sleeve. The sleeve is next inserted into the fistula so that the second end of the sleeve lies in the esophagus. The second end of the sleeve is permitted to dissolve in place so that the first means returns to undeformed orientation in the esophagus.

Illustratively according to this aspect of the invention, the first means comprises one or more of the coils formed to extend radially outward from the coil axis beyond the generally circular projection of the coils onto the first end.

According to still another aspect of the invention, a method is provided for constructing a one-way valve having a seat and a closure having a position against the seat to prevent flow in one direction therethrough and a position away from the seat to promote flow in the other direction therethrough. The method comprises the steps of providing a sheet of a resilient, flexible material having first and second oppositely facing sides, mounting the sheet of resilient, flexible material adjacent the seat, providing first and second sheets of a more rigid material, sandwiching the sheet of resilient, flexible material between the first and second sheets of more rigid material, and joining the first and second sheets of more rigid material together.

Illustratively according to this aspect of the invention, the step of sandwiching the sheet of resilient, flexible material between the first and second sheets of more rigid material comprises the steps of relieving a region on one side of one of the sheets of more rigid material corresponding to the shape of a region of the sheet of resilient, flexible material, and placing the region of the sheet of resilient, flexible material in the relieved region of the sheet of more rigid material prior to the step of attaching the first and second sheets of more rigid material together.

Additionally illustratively according to this aspect of the invention, the relieved region of the first sheet of more rigid material is offset from an edge of the first sheet of more rigid material, and the second sheet of more rigid material is not offset from the edge of the first sheet of more rigid material when the first and second sheets of more rigid material are joined together. The step of joining the first and second sheets of more rigid material together comprises the step of joining the first and second sheets of more rigid material together adjacent the edge to enclose an edge of the sheet of resilient flexible material.

According to still another aspect of the invention, a voice prosthesis device for mounting in a tracheoesophageal fistula is constructed substantially completely from a biocompatible metal. The voice prosthesis device includes a cylinder having an axis, a first end for positioning in the esophagus of a wearer and a second end for positioning in the trachea of the wearer. The cylinder includes means defining a passageway therethrough between the first and second ends thereof. A one-way valve is provided within the passageway and a flange extends radially outwardly adjacent the second end of the cylinder. The one-way valve includes a valve seat facing the first end and extending radially inwardly into the passageway. A valve closure is provided for seating against the seat. The valve closure is attached in operative position within the passageway adjacent the seat. The closure includes a sheet of resilient, flexible biocompatible material for providing a hinge. The sheet of resilient, flexible biocompatible material has a first surface facing toward the seat and an opposed second surface facing toward the first end of the voice prosthesis device. Sheets of biocompatible metal are provided for shielding the first and second surfaces of the sheet of resilient, flexible biocompatible material.

According to this aspect of the invention, the sheets of biocompatible metal include a first sheet of biocompatible metal or mounting on the side of the sheet of resilient, flexible biocompatible material facing the seat. The first sheet has a first side facing the seat and a second side facing away from the seat. A second sheet of biocompatible metal is mounted on the side of the sheet of resilient, flexible biocompatible material facing the first end. The second sheet has a first side facing the first end and a second side facing the seat. One of the biocompatible metal sheets' second sides includes a relief having a shape corresponding to the shape of a region of the sheet of resilient, flexible biocompatible material for receiving the region of the sheet of resilient, flexible biocompatible material and for holding the region of the sheet of resilient, flexible biocompatible material between the first and second sheets of biocompatible metal when the second sides of the first and second sheets of biocompatible metal are joined to capture the sheet of resilient flexible biocompatible material therebetween.

Illustratively according to this aspect of the invention, the relief is offset from an edge of the second side, and the other of the first and second sheets of metal is not offset from the edge, so that when the first and second sheets of metal are joined together to shield the first and second surfaces of the sheet of resilient flexible biocompatible material, an edge of the sheet of resilient flexible biocompatible material is enclosed.

The invention may best be understood by referring to the following description and accompanying drawings which illustrate the invention. In the drawings.

Figure 1:
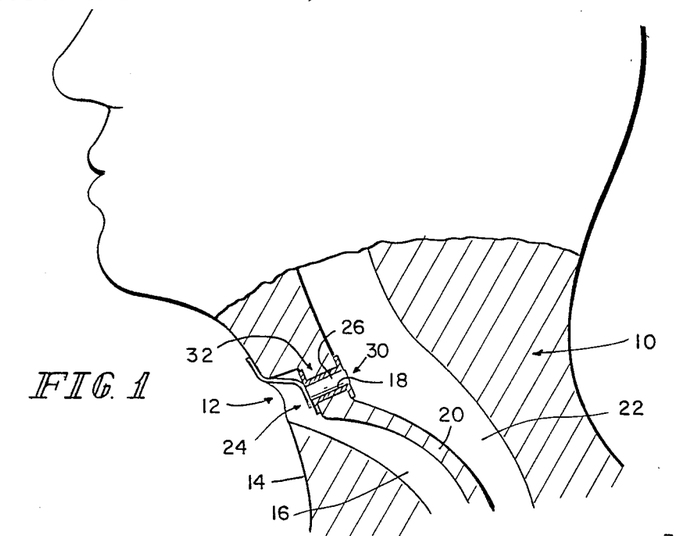
FIG. 1 illustrates a partly cut away side elevational view of a portion of a human head and neck showing the location of a device of the present invention.

Turning now to FIG. 1, a laryngectomee 10 is provided with a tracheostoma 12 opening from the outside of his neck 14 to his trachea 16. In an operation to restore his voice, a puncture establishes a fistula 18 through the wall 20 of tissue that separates his trachea 16 from his esophagus 22. In the prior art, a voice prosthesis device of the general type of those noted above was inserted into the fistula 18. When the laryngectomee 10 desired to speak, he had only to occlude his tracheostoma 12 with his finger or through the action of a device of the type described in Blom et al U.S.S.N. No. 316,055, filed Oct. 29, 1981 and assigned to the same assignee as this application. This permitted air from the trachea 16 to be channeled into one end 24 of the voice prosthesis device 26, through the one-way valve 28 adjacent the other end 30 of device 26 and into the esophagus 22, permitting tracheo-esophageal speech.

Figures 2, 3, 4:
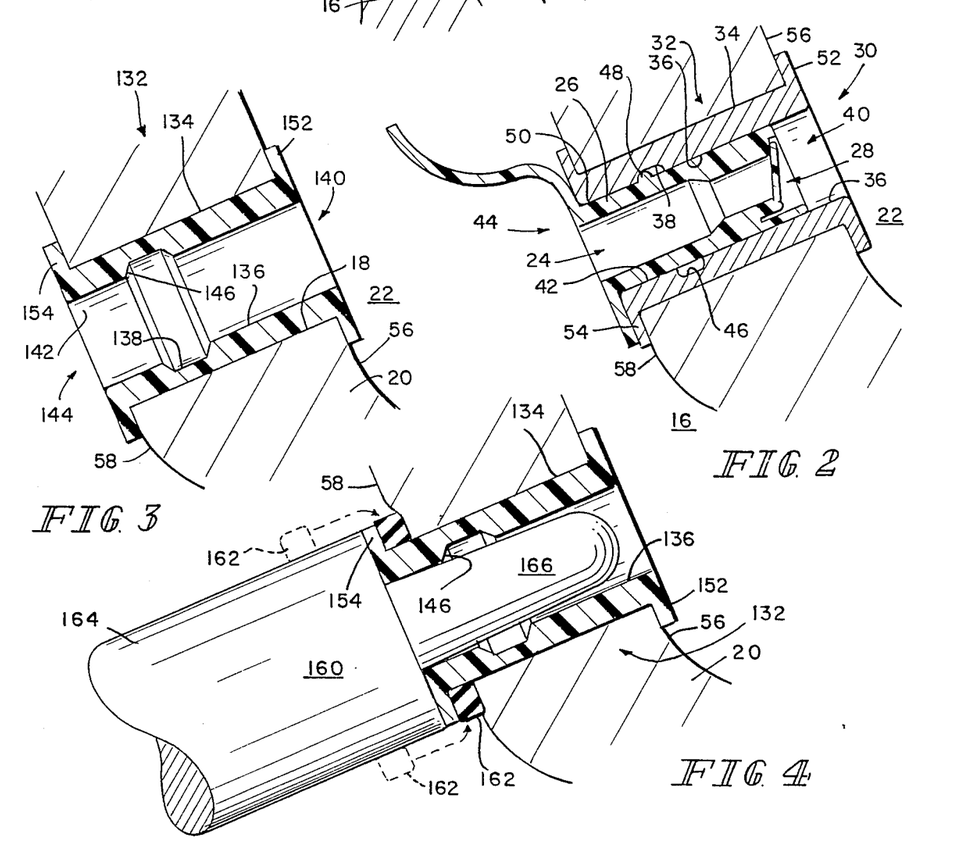
FIG. 2 illustrates a greatly enlarged sectional side elevational view of a detail of FIG. 1.
FIG. 3 illustrates an enlarged sectional side elevational view of an alternative construction of the device of FIG. 2.
FIG. 4 illustrates an enlarged sectional side elevational view of another construction of the device of FIG. 2, showing a tool and spacer for use with the devices of FIGS. 1-4.

According to the invention, to facilitate hygiene and replacement of the device 26, a surgical implant 32 is positioned in the fistula 18 when the fistula 18 is originally formed or punctured through the wall 20. The implant 32 comprises an outer cylindrical wall 34 and an inner cylindrical wall 36. The inner cylindrical wall 36 is divided into a first, larger diameter portion 38 positioned toward the esophageal end 40 and a second, smaller diameter portion 42 positioned toward the tracheal end 44 of implant 32. Larger diameter portion 38 illustratively is in the form of a groove which extends around wall 36. An intermediate portion 46 between portions 38 and 42 is formed as a curved region 46. This intermediate portion cooperates with a radially outwardly extending projection 48 formed on the outer cylindrical side wall 50 of voice prosthesis device 26 to secure device 26 within implant 32. Because device 26 is typically constructed from a relatively soft, pliable and resilient silicone material, it is relatively simple to snap device 26 into and out of engagement in implant 32 for hygiene and replacement purposes.

A radially outwardly extending flange 52 is provided at the esophageal end 40 of surgical implant 32, and a radially outwardly extending flange 54 is provided at the tracheal end 44 of implant 32. When implant 32 is positioned in the fistula, flange 52 lies adjacent the anterior wall 56 of the esophagus 22 and flange 54 lies adjacent the posterior wall 58 of the trachea 16.

In the embodiment of FIG. 3, a surgical implant 132 is positioned in the fistula 18 when the fistula 18 is originally formed or punctured through the wall 20. The implant 132 comprises an outer cylindrical wall 13 and an inner cylindrical wall 136. The inner cylindrical wall 136 is divided into a first, larger diameter portion 138 positioned toward the esophageal end 140 and a second, smaller diameter portion 142 positioned toward the tracheal end 144 of implant 132. Larger diameter portion 138 illustratively is in the form of a groove which extends around wall 136. An intermediate portion 146 between portions 338 and 142 is formed as a tapered region 146. This intermediate portion cooperates with the radially outwardly extending projection 48 formed on the outer cylindrical side wall 50 of voice prosthesis device 26 to secure device 26 within implant 132. Because device 26 is typically constructed from a relatively soft, pliable and resilient silicone material, it is relatively simple to snap device 26 into and out of engagement in implant 132 for hygiene and replacement purposes.

A radially outwardly extending flange 152 is provided at the esophageal end 140 of surgical implant 132, and a radially outwardly extending flange 154 is provided at the tracheal end 144 of implant 132. When implant 132 is positioned in the fistula, flange 152 lies adjacent the anterior wall 56 of the esophagus 22 and flange 154 lies adjacent the posterior wall 58 of the trachea 16.

There may be some edema of the wall 20 as a result of placement of the implant 32 or 132. Referring to FIG. 4, to compensate for this edema, a tool 160 and resilient rings 162 of a biocompatible material such as soft silicone are provided. The rings 162 are expanded and slipped over the enlarged portion 164 of the tool adjacent its end 166 remote from its handle (not shown). The remote end 166 is slipped into the implant 32, 132 and a ring 162 is worked off the enlarged portion 164, which has the same size as the flange 54 or 154, over the flange 54, 154 and onto the exterior wall 34, 134 of the implant 32, 132. Ring 162 acts as a spacer between the flange 54, 154 and the posterior wall 58 of the trachea to prevent implant 32, 132 from sliding back and forth in fistula 18 after the edema has subsided. Because there may be varying degrees of edema, different thickness rings 162 can be provided.

Figure 5:
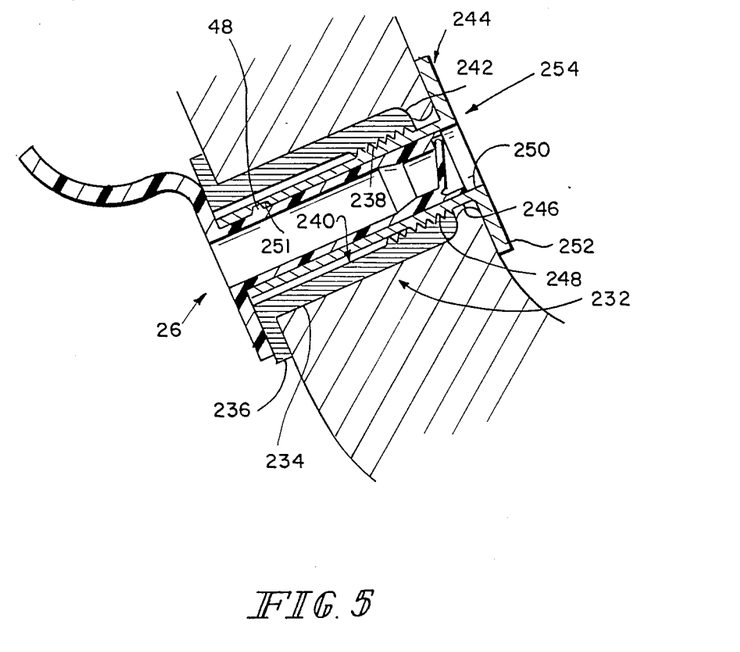
FIG. 5 illustrates an enlarged sectional side elevational view of another construction of the device of FIGS. 2-4.
Figure 6:
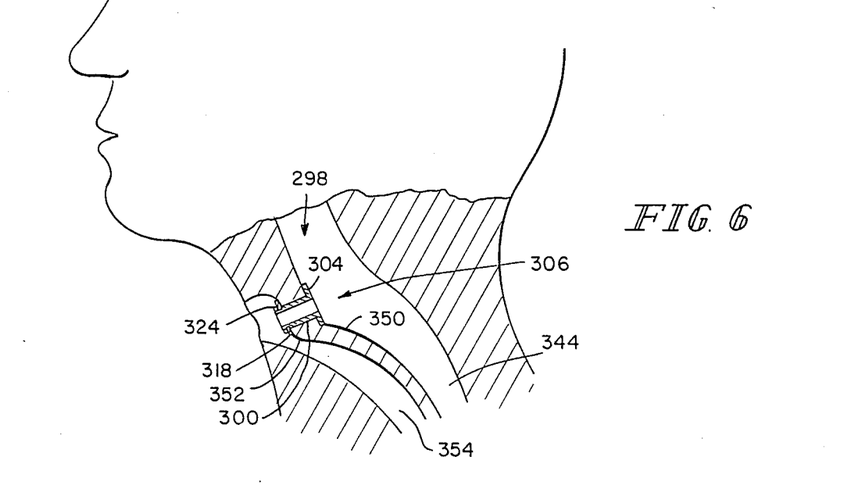
FIG. 6 illustrates a partly cut away side elevational view of a portion of a human head and neck showing the location of a device of the present invention.

In the embodiment of the invention illustrated in FIG. 5, an implant 232 comprises a first cylindrical female member 234 having a radially outwardly extending flange 236 at one ed and an interiorly threaded 238 right circular cylindrical passageway 240 extending through it from its flanged 236 end to its other end 242. Although passageway 240 extends completely through to the flanged 236 end, the threads 238 stop a short distance from end 242. Implant 232 also includes a male member 244 having a right circular cylindrical outer sidewall 246 which has threads 248 complementary to threads 238. Male member 244 includes a central passageway 250 and a radially outwardly extending flange 252 at its end 254. Passageway 240 is sized to receive a voice prosthesis device such as device 26 of FIGS. 1-2. The voice prosthesis device can be designed with a radial projection such as projection 48 of FIGS. 1-2, and a radial indentation 251 is provided in the passageway 240 of female member 234 for engagement by the projection to position the voice prosthesis device in passageway 240.

The embodiment of FIG. 5 is intended for use in those situations in which the thickness of the tracheoesophageal wall changes while the implant is in the tracheoesophageal puncture. If that happens, the male member 244 can be screwed into or out of the female member 234, depending upon whether the thickness of the tracheoesophageal wall around the puncture is decreasing or increasing. In this orientation, the distance between flanges 236, 252 equals the tracheoesophageal wall thickness.

In the embodiment of the invention illustrated in FIG. 5, an implant 232 comprises a first cylindrical female member 234 having a radially outwardly extending flange 236 at one end and an interiorly threaded 238 right circular cylindrical passageway 240 extending through it from its flanged 236 end to its other end 242. Although passageway 240 extends completely through to the flanged 236 end, the threads 238 stop a short distance from end 242. Implant 232 also includes a male member 244 having a right circular cylindrical outer sidewall 246 which has threads 248 complementary to threads 238. Male member 244 includes a central passageway 250 and a radially outwardly extending flange 252 at its end 254. Passageway 250 is sized to receive a voice prosthesis device such as device 26 of FIGS. 1-2. The voice prosthesis device can be designed with a radial projection such as projection 48 of FIGS. 1-2, and a radial indentation 251 is provided in the passageway 250 of male member 244 for engagement by the projection to position the voice prosthesis device in passageway 250.

The embodiment of FIG. 5 is intended for use in those situations in which the thickness of the tracheoesophageal wall changes while the implant is in the tracheoesophageal puncture. If that happens, the male member 244 can be screwed into or out of the female member 234, depending upon whether the thickness of the tracheoesophageal wall around the puncture is decreasing or increasing. In this orientation, the distance between flanges 236, 252 equals the tracheoesophageal wall thickness.

Figure 8:
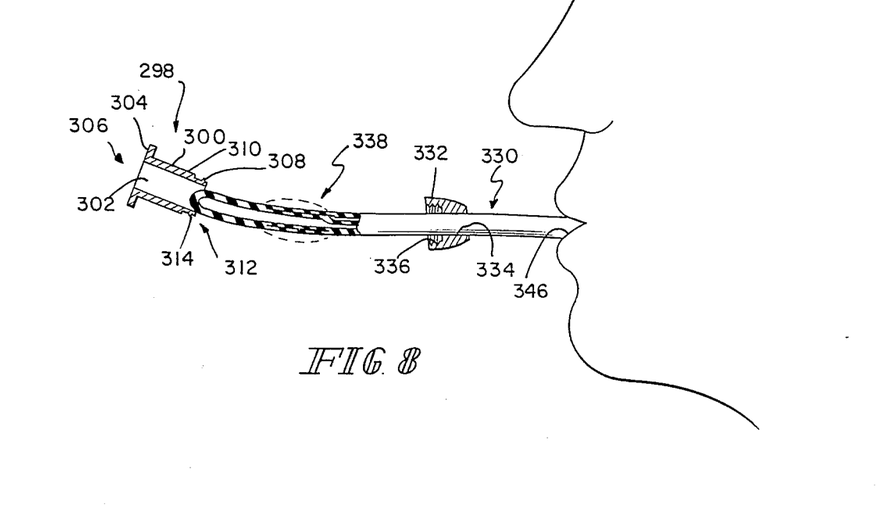
Figure 9:
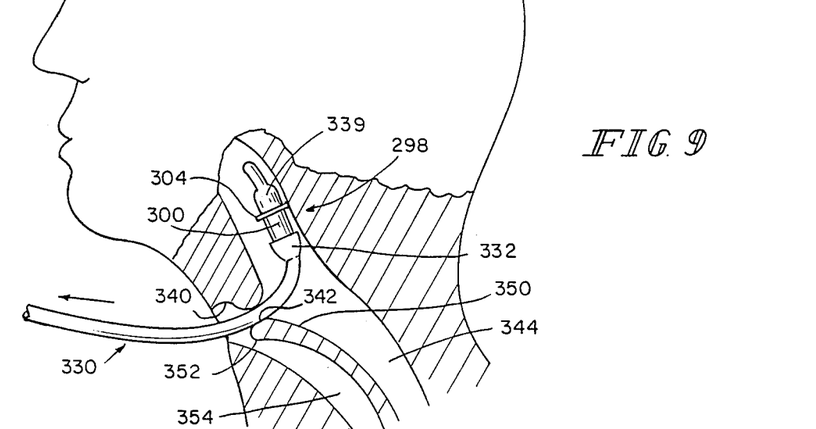
Figure 10:
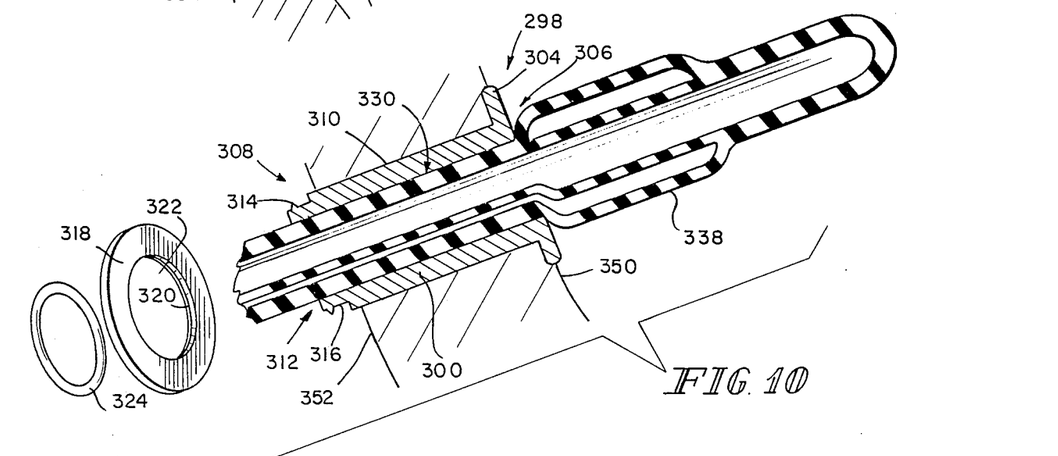
FIG. 10 illustrates an enlarged sectional side elevational view of a portion of a human neck showing a step in a surgical procedure to implant the device of FIG. 6.
Figure 11:
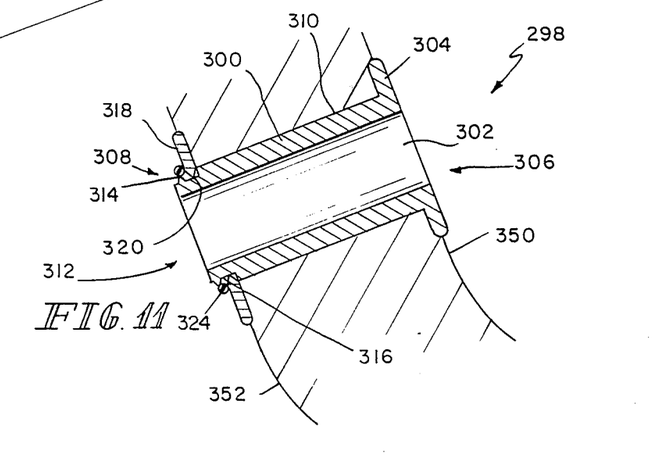
FIG. 11 illustrates an enlarged sectional side elevational view of the device of FIGS. 6-10 implanted in a human neck.

Another embodiment of the invention is illustrated along with a method for implantation in FIGS. 6-11. Referring particularly to FIGS. 10-11, the implant 298 includes a right circular cylindrical barrel 300 having an interior wall 302 and a radially outwardly extending flange 304 at one end 306 thereof. The region 308 of the exterior wall 310 of barrel 300 adjacent its other end 312 is threaded at 314 with only one or two threads. A grooved region 316 lies immediately adjacent the threads 314 between the threads 314 and flange 304. A washer 318 has a threaded 320 central aperture 322, the threads 320 of which are the same as threads 314. A small elastomeric O-ring 324 is sufficiently elastic to permit it to be stretched to a large enough diameter to fit onto end 312.

Figure 7:
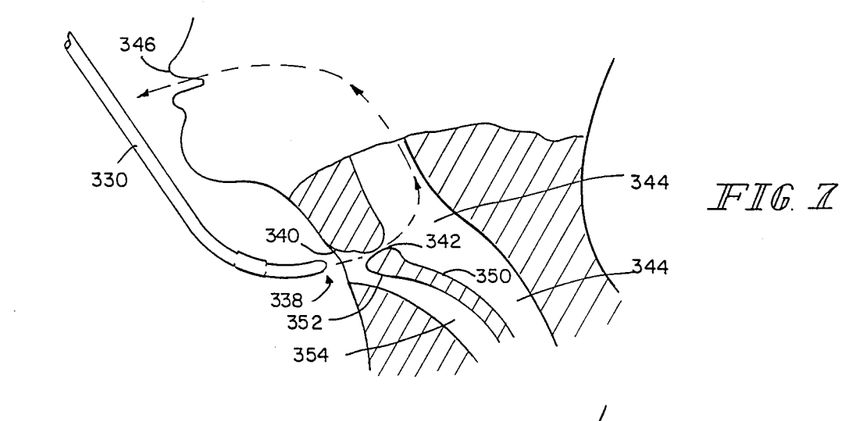
FIGS. 7-9 illustrate partly cut away side elevational views of a portion of a human head and neck showing steps in a surgical procedure to implant the device of FIG. 6.

Referring now to FIGS. 7-9, additional components which are useful in the implantation of implant 298 include a red rubber Foley catheter 330 with a Cude tip and a somewhat bullet-shaped nut 332 having a central aperture 334 threaded 336 with the same threads as threads 314 and 320 (FIG. 8).

In the implantation method, the tip 338 of catheter 330 is first passed through the tracheostoma 340 and the puncture 342 and then upward through the esophagus 344 and out of the mouth 346 of the patient. See FIG. 7. The curved 338 Cude tip of catheter 330, illustrated in FIG. 7, aids in this step of the process. Referring to FIG. 8, the bullet-shaped nut 332 is then threaded onto tip 338, contoured end toward the patient's mouth 346. The implant 298 is then threaded onto tip 338 without washer 318 or 0-ring 324 installed, and with flange 304 directed away from the patient's mouth 346. The threads 314, 336 are engaged and threaded finger tight. The balloon tip 338 of catheter 330 is inflated, capturing the assembly 298, 332 on tip 338. Catheter 330 is then pulled (FIG. 9) back through puncture 342 and tracheostoma 340 until flange 304 lies against the anterior wall 350 f the esophagus 344.

Nut 332 is unscrewed from end 312 and threaded off catheter 330. Washer 318 is threaded onto catheter 330 and the threads 314 320 are engaged. Washer 318 is screwed onto threads 314 until threads 320 pass threads 314 completely and disengage from them and fall into groove 316. See FIG. 11. The length of the implant 298 has been chosen so that, at the time threads 320 pass threads 314 and fall into groove 316, washer 318 lies against the posterior wall 352 of the trachea 354. The implant 298 is thus in place ready to receive a low pressure voice prosthesis device such as device 26 of FIGS. 1-2. To reduce the possibility that threads 314, 320 might reengage, permitting washer 318 to back off end 312 and perhaps be lost, O-ring 324 is stretched over a suitable tool, not shown in FIGS. 6-11, the tool is inserted int barrel 300 and O-ring 324 is rolled off the tool onto threads 314, capturing washer 318 in groove 316. O-ring 324 is sized to be tightly stretched over end 312.

Implant 298 is constructed from polished titanium which, like stainless steel and Teflon, is biocompatible. Titanium is also about fifty percent lighter in weight than stainless steel.

Figure 12:
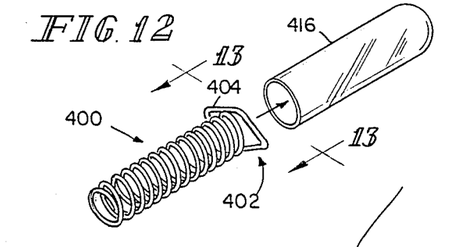
FIG. 12 illustrates an exploded perspective view of another device according to the present invention and half of a gelatin capsule which is useful in implanting the device of FIG. 12.
Figure 13:
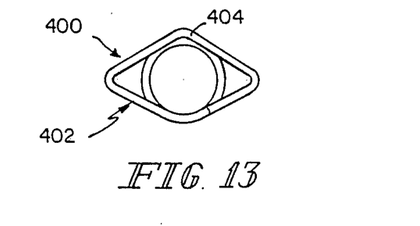
FIG. 13 illustrates an esophageal end view of the device of FIG. 12, taken generally along section lines 13—13 of FIG. 12.

FIG. 12 illustrates another embodiment of the surgical implant. The implant 400 of FIG. 12 is configured as a helical coil spring, the esophageal end 402 of which is deformed into somewhat of a diamond shape 404, as best illustrated in FIG. 13. The diamond shaped portion 404 replaces the esophageal end retaining flanges of the solid cylindrical implant embodiments of FIGS. 1-11. Although the portion 404 is illustrated as having a long axis and that long axis is illustrated as extending horizontally in FIGS. 12-13, it should be understood that in place the long axis may extend longitudinally of the esophagus. It should further be understood that the portion 404 may be more square than illustrated in FIGS. 12-13.

Figures 14, 15, 18:
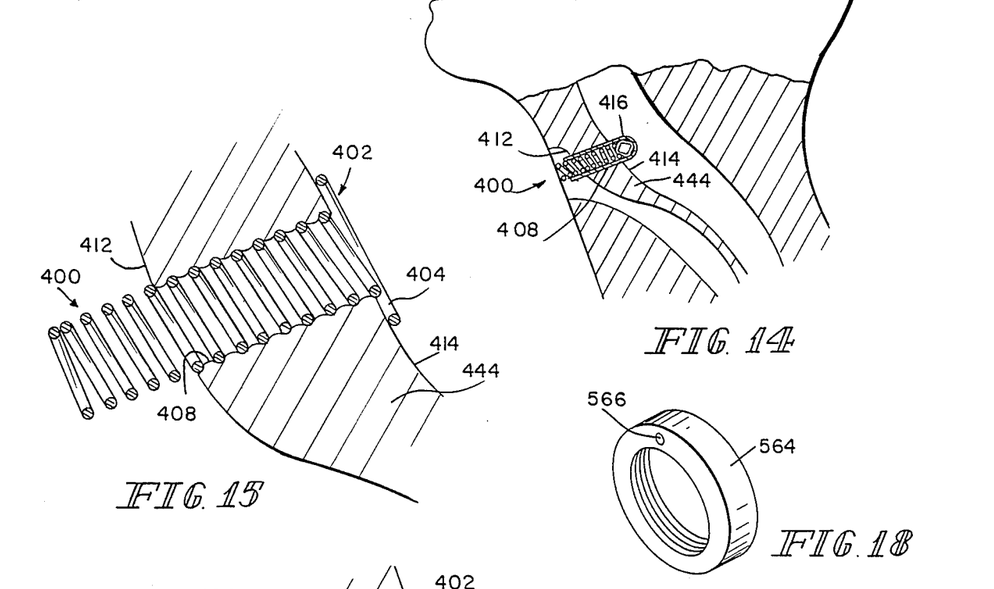
FIG. 14 illustrates a partly cut away side elevational view of a portion of a human head and neck showing the method of implantation and location of the device of FIGS. 12-13.
FIG. 15 illustrates a greatly enlarged sectional side elevational view of the implant of FIGS. 12-14 after dissolution of the gelatin capsule half.
FIG. 18 illustrates a greatly enlarged perspective view of another type of retaining nut for use with the implant of FIGS. 12-15.

FIGS. 12 and 14 illustrate a method of implantation of the helical spring surgical implant 400. The fistula 408 is formed in the usual manner between the posterior wall 412 of the trachea and the anterior wall 414 of the esophagus. Then end portion 404 of implant 400 is deflected sufficiently to insert it into half 416 of a gelatin capsule. Implant 400 is inserted as far as it will go into capsule 416 and a standard insertion tool is then inserted into implant 400 and the implant is inserted into the fistula 408. Saliva and mucus dissolve the half gelatin capsule 416 and end portion 404 springs back to its undeflected orientation. The final steps in completing the implantation depend upon what kind of voice prosthesis device ultimately will be used in the implant 400.

Figure 16:
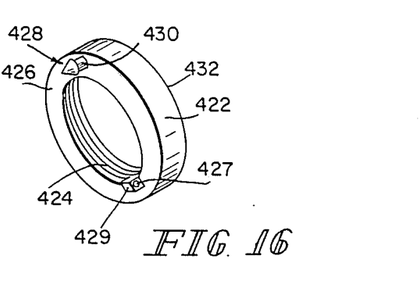
FIG. 16 illustrates a greatly enlarged perspective view of one type of retaining nut for use with the implant of FIGS. 12-15.
Figure 17:
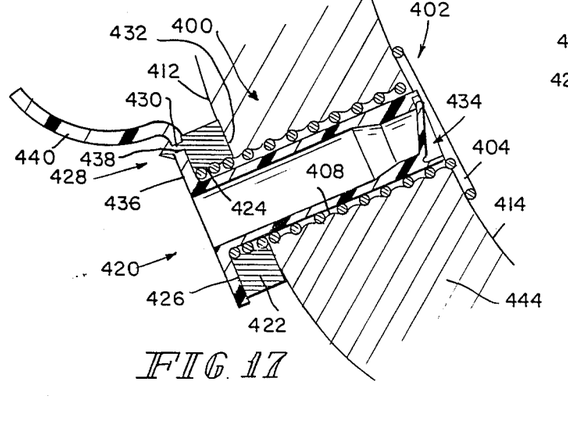
FIG. 17 illustrates a greatly enlarged sectional side elevational view of the implant of FIGS. 12-15 implanted in a tracheoesophageal fistula with the retaining nut of FIG. 16 on it and a soft silicone voice prosthesis device in place in it.

If a soft silicone prosthesis 420 of the type illustrated in FIG. 17 is to be used, a circular cross section nut 422 illustrated in FIG. 16 is used. Nut 422 includes a threaded center opening 424 the pitch of the threads of which corresponds generally to the pitch of the coils of implant 400. One 426 of the axial faces of nut 422 is provided with conically shaped process 428 on an axially extending, slightly smaller diameter shaft 430. Nut 422 is threaded onto the end of implant 400 that protrudes from the posterior wall 412 of the trachea until the axial surface 432 of nut 422 contacts the posterior wall 412 of the trachea. Nut 422 is then screwed on less than an additional turn so that process 428 is at the top. As the excess length of implant 400 protrudes beyond face 426, it is led through a somewhat circumferentially extending passageway 427 through a boss 429 formed on face 426 adjacent threaded center opening 424. This excess length is held and cut off adjacent where it protrudes from boss 429 using a wire cutter. This forms a burr (not shown) on the cut off end of implant 400. The burr keeps the nut 422 from backing off the end of implant 400. A soft silicone prosthesis 420 is then inserted into implant 400, valve end 434 first, until the flange 436 on the prosthesis 420 contacts face 426 of nut 422. Then process 428 is forced through a shaft 430-diameter hole 438 on the retaining strap 440 with which flange 436 is provided to capture prosthesis 420 in implant 400. The configuration, that is, as a helical coil spring, of implant 400 automatically compensates for any edema of the wall 444 between the trachea and esophagus by stretching. As the edema subsides, the implant goes back to its original undeflected orientation. If the wall 444 thickness shrinks, as sometimes happens, and the shrinkage appears to be permanent, the prosthesis 420 can be removed and nut 422 screwed onto implant 400 a little further. The excess length of implant 400 can be cut off in the same manner as previously described and prosthesis 420 then can be replaced.

If prosthesis 420 is constructed from a material having sufficient hardness characteristics, its outer sidewall can also be threaded for some portion of its length, with such threads engaging implant 400.

Figure 19:
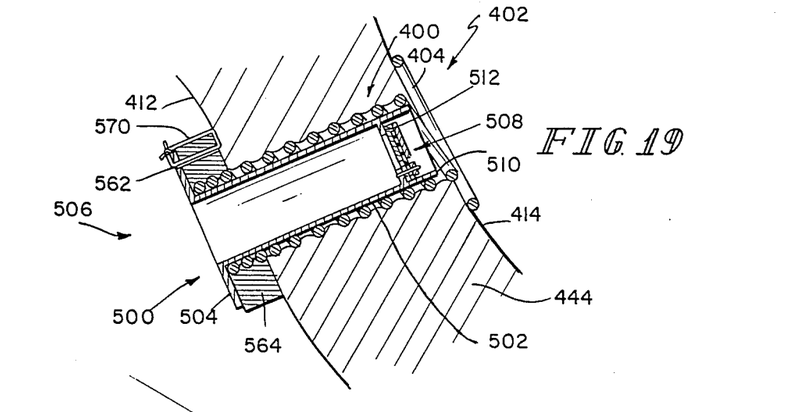
FIG. 19 illustrates a greatly enlarged sectional side elevational view of the implant of FIGS. 12-15 implanted in a tracheoesophageal fistula with the retaining nut of FIG. 18 on it and a substantially all-metal voice prosthesis device according to the present invention in place in it.
Figures 20, 21:
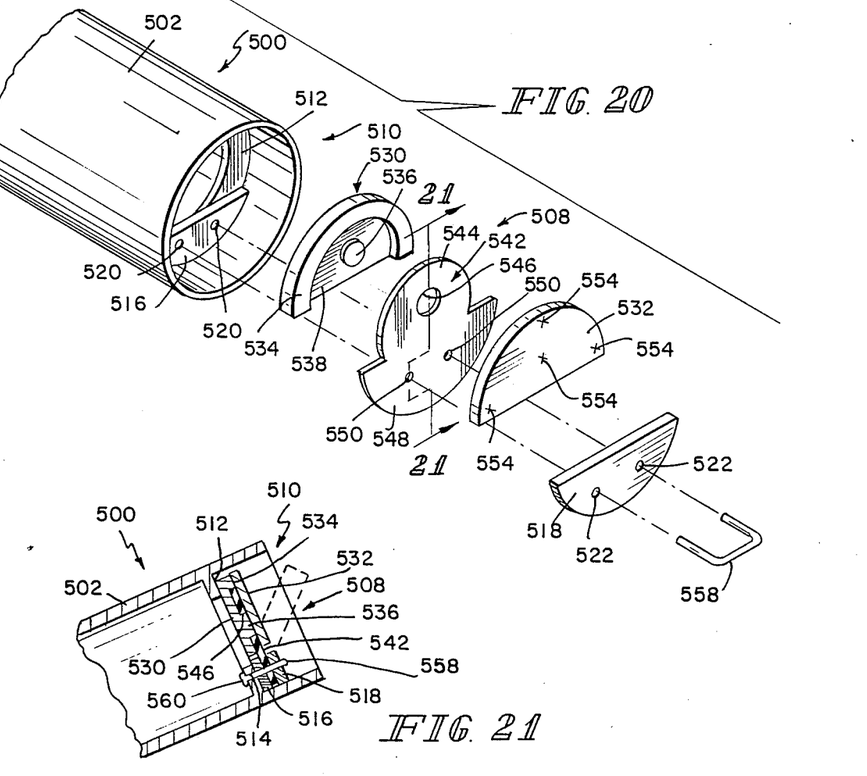
FIG. 20 illustrates a fragmentary exploded perspective view of the substantially all-metal voice prosthesis device of FIG. 19.
FIG. 21 illustrates an enlarged fragmentary sectional side elevational view of the substantially all-metal voice prosthesis device of FIGS. 19-20.

Recent experience has established that some patients have difficulty replacing a soft silicone prosthesis after cleaning, even in a surgical implant such as those described herein. In such cases, it is desirable to provide not only an implant that resists the growth of organisms such as those previously mentioned, but also to provide a voice prosthesis that resists growth of such organisms. To this end, the prosthesis 500 illustrated in FIGS. 19-21 is provided.

Prosthesis 500 is a substantially all-metal prosthesis. It includes a right circular cylinder 502 having an outside diameter only slightly smaller than the insider diameter of implant 400. Prosthesis 500 is provided with a flange 504 at the tracheal end 506 of cylinder 502. A recessed one-way valve 508 is provided within the cylinder 502 adjacent the esophageal end 510 thereof. Valve 508 includes a seat 512 which extends radially inwardly from the inner sidewall of cylinder 502. Two spaced holes 514 are provided in the region of seat 512 adjacent the bottom thereof. Two somewhat D-shaped pieces 516, 518 of 0.005 inch (0.127 mm) thick medical grade stainless steel are provided with matching pairs 520, 522, respectively, of spaced holes. Two other somewhat D-shaped pieces 530,, 532 of medical grade stainless steel are also provided. Pieces 530, 532 are complementarily shaped to pieces 516, 518, respectively, to form circles with substantially the same size as the interior transverse section of cylinder 502. Piece 530 is made from a 0.010 inch (0.254 mm) blank which is chemically etched to provide an arcuate circumferentially extending land 534 and a circular land 536. Lands 534, 536 remain the original 0.010 inch (0.254 mm) thickness of the blank. The remaining portion 538 of piece 530 is etched to a thickness of 0.005 inch (0.127 mm). Piece 532 is a uniform 0.005 inch (0.127 mm) thickness. A 0.005 inch (0.127 mm) thick piece 542 of medical grade silicone sheet, which can be fiber reinforced, has an upper portion 544 of the same shape as portion 538, including a hole 546, and a lower portion 548 of the same general configuration as pieces 516, 518, including a pair 550 of holes spaced on the same spacing as the holes or pairs 514, 520 and 522.

The valve 508 is assembled by placing upper portion 544 in portion 538 with hole 546 accommodating land 536, laying piece 532 over piece 530 and laser beam welding pieces 530, 532 together illustratively at four locations 554. This captures piece 542 between pieces 530, 532. Piece 516 is placed against the esophageal side of seat 512 with holes 514, 520 in alignment. The assembly of pieces 530, 532, 542 is then inserted into the esophageal end 510 of cylinder 502 and holes 550 aligned with holes 514, 520. Next, piece 518 is inserted into the esophageal end 510 and its holes 522 aligned with holes 514, 520, 550. A wire staple 558 is inserted either from the tracheal end 506 or from the esophageal end 510 through aligned pairs 514, 520, 522, 550 of holes and the staple ends 560 are mushroomed using a laser beam. The resulting hinge, although formed using silicone sheet material 542, presents essentially only stainless steel surfaces of pieces 516, 518, 530, 532 for colonization by organisms, and the organisms generally are very poor at colonizing medical grade stainless steel. The same is true of titanium which can be substituted for medical grade stainless steel in prosthesis 500. This is believed to be due to the substantially reduced porosity and pore size of the metals compared to that of silicone. These organisms, if permitted to colonize a silicone voice prosthesis, deformed the one-way valve member of the prosthesis to the extent that it would no longer seat to perform its valving function. This could occur in some patients in as short a time as five days. This, of course, rendered the prosthesis unuseable, requiring it to be replaced.

In order to fit prosthesis 500 substantially permanently into implant 400, flange 504 is provided with a hole 562. A nut 564, illustrated in FIG. 18, is provided with a hole 566. If the all metal prosthesis 500 is to be used in the implant 40, nut 564 is used instead of nut 422 of FIG. 16. Nut 564 is placed on implant 400 in the same manner as described in connection with nut 422. Prosthesis 500 is fitted into implant 400 with holes 562, 566 aligned. A single suture 500 is taken through holes 562, 566 and tied, capturing prosthesis 500 in implant 400.

The outer sidewall of cylinder 502 can be threaded along some portion of its length, with such threads engaging implant 400.

What is claimed is:

1. In combination, a surgical implant and voice prosthetic device for use in voice restoration, the implant comprising multiple coils of a resilient material, the coils defining an axis and two ends, first means provided at a first end for positioning adjacent the anterior wall of the esophagus of a wearer of the surgical implant, and second means comprising a nut having a passageway for receiving at least one of said coils, said passageway having internal threads for threadably engaging said at least one coil, and wherein said second means is provided at a second end for positioning adjacent the posterior wall of the trachea of the wearer said voice prosthetic further comprising a cylinder defining an axis, a first end for positioning adjacent said first end of the coils and a second end for positioning adjacent said second end of the coils, the cylinder including means defining a passageway therethrough between said first and second ends thereof, means providing a one-way valve within said voice prosthesis device passageway and a flange extending radially outwardly adjacent said second end of said voice prosthesis device cylinder, said voice prosthesis device flange comprising two opposed faces, a first of which faces axially of said voice prosthesis device toward the posterior wall of the trachea when the voice prosthesis device is positioned in the implant and a second of which faces axially of said voice prosthesis device away from the posterior wall of the trachea when the voice prosthesis device is positioned in the implant.

2. The apparatus of claim 1 wherein the nut comprises two opposed faces, a first of which faces axially of said coils toward the posterior wall of the trachea when the nut threadably engages said at least one coil, and a second of which faces axially of said coils away from the posterior wall of the trachea when the nut threadably engages said at least one coil.

3. The apparatus of claim 2 wherein said nut further comprises means providing a second passageway extending between the first and second faces thereof.

4. The apparatus of claim 3 wherein said voice prosthesis device flange includes means defining a passageway extending therethrough between said first and second faces of said voice prosthesis device flange.

5. The apparatus of claim 4 wherein the voice prosthesis device cylinder and flange are constructed from a biocompatible metal and the voice prosthesis device one-way valve comprises a valve seat facing said first end and extending radially inwardly of said voice prosthesis device cylinder into said voice prosthesis device passageway, a valve closure for seating against said one-way valve seat, and means for attaching said valve closure in operative position within said voice prosthesis device passageway adjacent said one-way valve seat.

6. The apparatus of claim 5 wherein said one-way valve closure comprises a sheet of resilient, flexible biocompatible material for providing a hinge, the sheet of resilient, flexible biocompatible material having a first surface facing toward said one-way valve seat and an opposed second surface facing toward said first end of said voice prosthesis device, and sheets of biocompatible metal for shielding said first and second surfaces of the sheet of resilient flexible biocompatible material.

7. A voice prosthesis device for mounting in a tracheoesophageal fistula, the voice prosthesis device constructed substantially completely from a biocompatible metal and including a cylinder having an axis, a first end for positioning i the esophagus of a wearer and a second end for positioning in the trachea of the wearer, the cylinder including means defining a passageway therethrough between said first and second ends thereof, means providing a one-way valve within said passageway and a flange extending radially outwardly adjacent said second end of said cylinder, the one-way valve including a valve seat facing said first end and extending radially inwardly into said passageway, a valve closure for seating against said seat and means for attaching said valve closure in operative position within said passageway adjacent said seat, said closure including a sheet of resilient, flexible biocompatible material for providing a hinge, the sheet of resilient, flexible biocompatible material having a first surface facing toward said seat and an opposed second surface facing toward said first end of said voice prosthesis device, and sheets of biocompatible metal overlying and shielding said first and second surfaces of the sheet of resilient, flexible biocompatible material, wherein said shielding acts to suppress the growth of organisms which otherwise would degrade the function of the valve.

8. The apparatus of claim 7 wherein the sheets of biocompatible metal comprise a first sheet of biocompatible metal for mounting on the side of the sheet of resilient, flexible biocompatible material facing the seat, the first sheet having a first side facing the seat and a second side facing away from the seat, a second sheet of biocompatible metal for mounting on the side of the sheet of resilient, flexible biocompatible material facing the first end, the second sheet having a first side facing the first end and a second side facing the seat, one of the biocompatible metal sheets second side including means defining a relief therein having a shape corresponding to the shape of a region of the sheet of resilient, flexible biocompatible material for receiving said region of the sheet of resilient, flexible biocompatible material and for holding said region of the sheet of resilient, flexible biocompatible material between the first and second sheets of biocompatible metal when the second sides of the first and second sheets of biocompatible metal are joined to capture the sheet of resilient flexible biocompatible material therebetween.

9. The apparatus of claim 8 wherein the relief is offset from an edge of the second side, and the other of the first and second sheets of metal is not offset from said edge so that when the first and second sheets of metal are joined together to shield the first and second surfaces of the sheet of resilient flexible biocompatible material, an edge of the sheet of resilient flexible biocompatible material is enclosed.

10. The apparatus of claim 9 and further comprising a third sheet of biocompatible metal for placing between the seat and the sheet of resilient flexible biocompatible material, and a fourth sheet of biocompatible metal for placing on the side of the sheet of resilient flexible biocompatible material opposite the side thereof facing the third sheet, and means for mounting the third sheet of biocompatible metal, the sheet of resilient, flexible biocompatible material and the fourth sheet of biocompatible metal all to the seat.

* * * * *

UNITED STATES PATENT AND TRADEMARK OFFICE
CERTIFICATE OF CORRECTION

PATENT NO. : 4,911,716

Page 1 of 2

DATED : March 27, 1990

INVENTOR(S) : Blom et al.

It is certified that error appears in the above-identified patent and that said Letters Patent is hereby corrected as shown below:

On the bibliography page, under "Other Publications", line 4, replace "Phinology" with --Rhinology--.

In column 5, line 19, replace "or" with --for--.

In column 5, line 27, replace "sheets'second" with --sheets' second--.

In column 7, line 26, replace "13" with --134--.

In column 7, line 34, replace "338" with --138--.

In column 8, line 4, replace "ed" with --end--.

In column 9, line 32, replace "f" with --of--.

In column 9, line 35, after "314", insert --,--.

In column 9, line 48, replace "int" with --into--.

In column 11, line 12, after "530", delete --,--

In column 11, line 66, replace "40" with --400--.

UNITED STATES PATENT AND TRADEMARK OFFICE
CERTIFICATE OF CORRECTION

PATENT NO. : 4,911,716
DATED : March 27, 1990
INVENTOR(S) : Blom et al.

It is certified that error appears in the above-identified patent and that said Letters Patent is hereby corrected as shown below:

In column 13, line 7, replace "i" with --in--.

In column 14, line 5, replace "side" with --sides--.

In column 14, line 5, "sheets" should be --sheets'--.

Signed and Sealed this

Twenty-fifth Day of June, 1991

Attest:

HARRY F. MANBECK, JR.

*Attesting Officer*  *Commissioner of Patents and Trademarks*